(12) United States Patent
Gonzalez

(10) Patent No.: US 11,646,112 B2
(45) Date of Patent: May 9, 2023

(54) REAL-TIME HEALTH CARE INVENTORY IMAGING AND TRACKING INTELLIGENCE SYSTEM

(71) Applicant: TaskUnite Inc., Santa Monica, CA (US)

(72) Inventor: Bianca Gonzalez, Santa Monica, CA (US)

(73) Assignee: TaskUnite Inc., Santa Monica, CA (US)

( * ) Notice: Subject to any disclaimer, the term of this patent is extended or adjusted under 35 U.S.C. 154(b) by 102 days.

(21) Appl. No.: 16/426,504

(22) Filed: May 30, 2019

(65) Prior Publication Data

US 2019/0371458 A1    Dec. 5, 2019

Related U.S. Application Data

(60) Provisional application No. 62/677,929, filed on May 30, 2018.

(51) Int. Cl.
*G16H 40/40* (2018.01)
*G16H 40/60* (2018.01)
(Continued)

(52) U.S. Cl.
CPC ........... *G16H 40/40* (2018.01); *G06Q 10/087* (2013.01); *G16H 40/60* (2018.01); *G06N 20/00* (2019.01); *G16H 30/20* (2018.01)

(58) Field of Classification Search
CPC ... G06F 1/00–2221/2153; G16H 10/00–80/00; G06N 3/00–99/007
See application file for complete search history.

(56) References Cited

U.S. PATENT DOCUMENTS 8,353,456 B2 * 1/2013 Jackson ................. B25H 3/028
                                                          235/454
9,415,935 B1 * 8/2016 Macfarlane .......... G06Q 10/087
(Continued)

FOREIGN PATENT DOCUMENTS

WO    WO-2014078860 A1 *  5/2014  ............. G06K 17/00

OTHER PUBLICATIONS

International Search Report in corresponding International Patent Application No. PCT/US2019/034616, dated Sep. 23, 2019, 12 pages.

*Primary Examiner* — Jonathon A. Szumny
(74) *Attorney, Agent, or Firm* — Young Basile Hanlon & MacFarlane, P.C.

(57) ABSTRACT

An imaging and tracking device used for real-time health care inventory intelligence includes an image sensor and a processor. The image sensor captures images of inventory items stored within a furniture unit to which at least a portion of the imaging and tracking device is coupled. The processor processes the images captured using the image sensor to detect a physical retrieval of one of the inventory items from the furniture unit and to generate a signal including data associated with the retrieved inventory item. A software application running on a server device uses the signal to automatically update a database record associated with the retrieved inventory item within a database. Information associated with the updated database record is then transmitted to a client device in communication with the server device. The information may include instructions for rendering a graphical user interface of the software application at the client device.

20 Claims, 8 Drawing Sheets

(51) Int. Cl.
  *G06Q 10/08* (2012.01)
  *G06Q 10/087* (2023.01)
  *G16H 30/20* (2018.01)
  *G06N 20/00* (2019.01)

(56) References Cited

U.S. PATENT DOCUMENTS

| | | | |
|---|---|---|---|
| 10,169,660 B1* | 1/2019 | Ren | G06Q 10/087 |
| 10,528,840 B2* | 1/2020 | Bailey | G06K 9/00208 |
| 10,733,565 B1* | 8/2020 | Stephens | G06T 7/0004 |
| 2004/0211868 A1* | 10/2004 | Holmes | F16M 11/041 |
| | | | 248/231.71 |
| 2009/0048868 A1* | 2/2009 | Portnoy | G16Z 99/00 |
| | | | 705/2 |
| 2011/0153466 A1 | 6/2011 | Harish et al. | |
| 2014/0297487 A1* | 10/2014 | Bashkin | A47B 81/00 |
| | | | 705/28 |
| 2014/0337040 A1 | 11/2014 | Debusk et al. | |
| 2014/0350716 A1* | 11/2014 | Fly | B65G 1/02 |
| | | | 700/215 |
| 2015/0019391 A1* | 1/2015 | Kumar | G06Q 10/087 |
| | | | 705/28 |
| 2015/0095189 A1* | 4/2015 | Dharssi | G07G 1/0081 |
| | | | 705/26.8 |
| 2015/0262116 A1* | 9/2015 | Katircioglu | G06K 9/00771 |
| | | | 705/28 |
| 2017/0142373 A1* | 5/2017 | Black | H04W 64/00 |
| 2017/0147966 A1 | 5/2017 | Aversa et al. | |
| 2017/0217381 A1* | 8/2017 | Gilling | B60R 11/02 |
| 2018/0070909 A1* | 3/2018 | Kravis | A61B 6/587 |
| 2018/0319607 A1* | 11/2018 | Nemati | G05B 19/4189 |
| 2019/0182534 A1* | 6/2019 | Matsuoka | H04N 21/472 |
| 2019/0236530 A1* | 8/2019 | Cantrell | G06Q 20/203 |
| 2019/0339923 A1* | 11/2019 | Nel | H04L 67/12 |
| 2020/0394599 A1* | 12/2020 | Akatsuka | G06K 9/00671 |

* cited by examiner

Search for Supplies [search box] Search

STN#: 103936
Name: Typhoid Vi Polysaccharide Vaccine
Tradename: Typhim Vi
Manufacturer: Sanofi Pasteur SA
Reference Number: 22280101
Lot Number: L10314810
Expiration Date: 1/31/2020
Shelf Location: Pharmacy 4th floor Shelf B24

Reorder from Manufacturer
View All Inventory
View All Inventory Task Association
View Educational Guidelines

Current Quantity: 4
Turnover Time: 52 hrs

| Date | Quantity |
|---|---|
| 4/16/2018 | 7 |
| 4/17/2018 | 6 |
| 4/18/2018 | 6 |
| 4/19/2018 | 5 |
| 4/20/2018 | 5 |
| 4/21/2018 | 4 |
| 4/22/2018 | 4 |

[Bar chart: Quantity vs. Day, Monday 4/16/18 through Sunday 4/22/18]

Educational Guidelines Typhoid Vaccine

Precautions:
- For patients with bleeding disorders, this vaccine is given deep subcutaneous to reduce bleeding.
- Where more than one vaccine is administered at the same time, the vaccines should be given at different sites at least 2.5 cm apart.
- Vaccine should occur at least 2 weeks prior to potential exposure with Salmonella typhi.
- Vaccines must never be mixed with other vaccines/medications in the same syringe

Administration Steps:
1. Give the patient informed consent for vaccine administration and warn them of adverse effects
2. Shake syringe prior to use
3. Apply new sterile needle:
   Adults: 22-25 guage, 1-1 1/2" needle
   Pediatrics: 5/8-1 (16-25) deltoid
   Pediatrics: 1-1 1/4 (25-32) anterolateral thigh
4. Administer intramuscularly (IM) through deltoid region or anterolateral part of thigh at a 90 degree angle
5. Firm pressure with gauze should be applied to the injection site
6. Dispose of the syringe in a 'sharps' container per waste management protocol

FIG. 6

REAL-TIME HEALTH CARE INVENTORY IMAGING AND TRACKING INTELLIGENCE SYSTEM

CROSS REFERENCE TO RELATED APPLICATION(S)

This disclosure claims priority to and the benefit of U.S. Provisional Application Patent Ser. No. 62/677,929, filed May 30, 2018, the entire disclosure of which is herein incorporated by reference.

TECHNICAL FIELD

This disclosure relates to a real-time health care inventory imaging and tracking intelligence system, in particular, to a system for real-time monitoring, tracking, and analysis of inventory usage in the health care field based on imaging, motion, and/or other detections.

BACKGROUND

Inefficiencies in health care supply chain tracking and managing, such as those resulting from insufficient technical approaches or the lack of intelligent technical modeling, cost the health care industry millions of dollars annually. Examples of such inefficiencies include inventory leakages, inaccurate charge captures, poor or improper inventory tacking, item expirations, and high administrative costs incurred in supply reordering. Moreover, many supply usage associated with specific patient care, employee tasks, task metrics and characteristics, and administrative activities in health care settings remain undocumented. The lack of documentation makes it difficult for health care providers (e.g., clinics and hospitals) to analyze activity-based cost metrics and information relating to supply chain and inventory utilization. Furthermore, because real-time inventory usage information is unavailable, it is difficult for health care providers to effectively improve staff operations.

SUMMARY

Disclosed herein are, inter alia, implementations of systems and techniques for real-time health care inventory imaging and tracking intelligence.

In one implementation, a system for real-time health care inventory tracking is disclosed. The system includes an imaging and tracking device and a server device. The imaging and tracking device includes an image sensor and a processor. The image sensor captures images of inventory items stored within a furniture unit to which at least a portion of the imaging and tracking device is coupled. The processor processes the images captured using the image sensor to detect a physical retrieval of one of the inventory items from the furniture unit and to generate a signal including data associated with the retrieved inventory item. The server device runs a software application that identifies the retrieved inventory item based on the signal. The software application uses the signal to automatically update a database record associated with the retrieved inventory item within a database. Information associated with the updated database record is transmitted to a client device in communication with the server device.

In another implementation, an imaging and tracking device for real-time health care inventory tracking is disclosed. The imaging and tracking device includes an image sensor, a processor, and a network interface. The image sensor captures images of inventory items stored within a furniture unit to which at least a portion of the imaging and tracking device is coupled. The processor processes the images captured using the image sensor to detect a physical retrieval of one of the inventory items from the furniture unit and to generate a signal including data identifying the retrieved inventory item. The network interface transmits the signal to a server device. A software application running on the server device uses the signal to automatically update a record associated with the retrieved inventory item within a database.

In yet another implementation, a method for real-time health care inventory tracking using an imaging and tracking device is disclosed. The method includes configuring the imaging and tracking device for use in tracking inventory items within a furniture unit. Using the imaging and tracking device, a physical retrieval of one of the inventory items from the furniture unit is detected. A first signal including data associated with the retrieved inventory item is generated at the imaging and tracking device. The first signal is transmitted from the imaging and tracking device to a server device running a software application for the real-time health care inventory tracking. The software application automatically updates a database record associated with the retrieved inventory item based on the first signal. The server device transmits a second signal indicative of the updated database record to a client device.

BRIEF DESCRIPTION OF THE DRAWINGS

The disclosure is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

FIG. 6 is an illustration showing an example of a graphical user interface (GUI) of a software application for inventory tracking and management.

DETAILED DESCRIPTION

Figure 1:
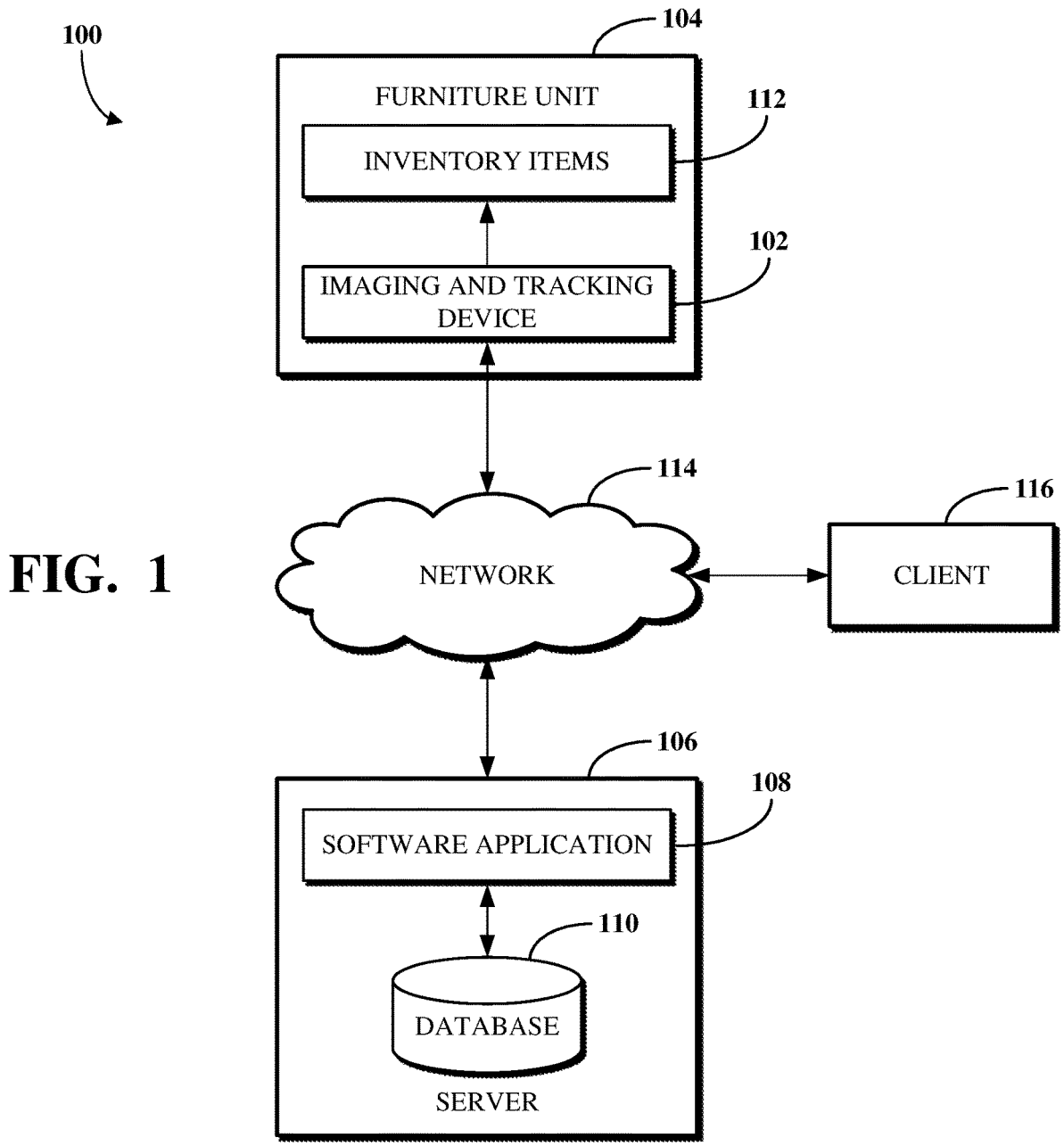
FIG. 1 is a block diagram showing an example of a real-time health care inventory imaging and tracking intelligence system.

Implementations of this disclosure include using an imaging and tracking device used for real-time health care inventory intelligence. The imaging and tracking device includes an image sensor and a processor. The image sensor captures images of inventory items stored within a furniture unit to which at least a portion of the imaging and tracking device is coupled. The processor processes the images captured using the image sensor to detect a physical retrieval of one of the inventory items from the furniture unit and to generate a signal including data associated with the retrieved inventory item. A software application running on a server device uses the signal to automatically update a database record associated with the retrieved inventory item within a database. Information associated with the updated database record is then transmitted to a client device in communication with the server device. The information may include instructions for rendering a graphical user interface of the software application at the client device.

An imaging and tracking device as disclosed herein is capable of capturing information indicative of a current inventory quantity within or on a furniture unit in real-time through one or more sensors (e.g., an image sensor, a motion sensor, or another sensor, or a combination thereof). For example, the sensors may be used to recognize inventory items stored within or on the furniture unit based on detected appearances of the inventory items (e.g., item shapes, text content, graphic content, item sizes, or the like) and/or locations of those inventory items within or on the furniture unit. Information recorded using the sensors is used in real-time to detect a physical retrieval of an inventory item from the furniture unit. For example, in some implementations, enumerations of the inventory items stored within or on the furniture unit may be used to detect a physical retrieval of an inventory item from the furniture unit. The detection of the physical retrieval of the inventory item is used in an automated updating of a database record by a software application to enable real-time tracking of the inventory item.

The real-time detection of changes to inventory items stored within or on a furniture item represents an improvement in inventory tracking computing technology, for example, based on the sensors included within the imaging and tracking device, the processing capabilities of the imaging and tracking device and/or of the server which runs the software application (e.g., in enumerating inventory items using real-time image data and detecting changes to inventory items based on such enumerations), and based on other improvements demonstrated throughout this disclosure. The updating of database records associated with inventory items detected to have changed (e.g., by a physical retrieval thereof from a furniture unit) further represents a solution rooted in the technical environment presented by the imaging and tracking device and communicated server to the technical problem of supporting real-time tracking.

To describe some implementations in greater detail, reference is first made to examples of hardware and software structures used to implement a real-time health care inventory imaging and tracking intelligence system. FIG. 1 is a block diagram showing an example of a real-time health care inventory imaging and tracking intelligence system 100. The system 100 includes an image and tracking device 102 coupled to a furniture unit 104 and a server 106 that runs a software application 108 and stores a database 110.

The imaging and tracking device 102 is a device which is used to monitor inventory items 112 stored within or on the furniture unit 104. The furniture unit 104 is or includes a piece of furniture with at least one surface configured for storing the inventory items 112. In some implementations, the furniture unit 104 may include a number of shelves of the same or different sizes. In some implementations, the furniture unit 104 may include a number of drawers of the same or different sizes. In some implementations, the furniture unit may include a number of cabinets of the same or different sizes. In some implementations, the furniture unit 104 may include a combination of shelves, drawers, and/or cabinets. The furniture unit 104 may be configured to store the inventory items 112 at particular temperatures. For example, the furniture unit 104 may be a refrigerated unit. In another example, the furniture unit 104 may be a heated unit. It will be understood that, aside from the foregoing examples and implementations, the furniture unit 104 may be include other types of open or enclosed surfaces or sets of surfaces within or upon which the inventory items 112 may be stored.

The inventory items 112 are items which may be used to provide health care support to a patient. Examples of the inventory items 112 include, but are not limited to, bandages, gauze materials, syringes, medications, ointments, needles, intravenous delivery mechanisms, fluids, medical tapes, and other materials. The inventory items 112 are stored within or on the furniture unit 104. For example, where the furniture unit 104 is a shelving unit with a number of shelves, each shelf of the furniture unit 104 can store some of the inventory items 112. In another example, some of the inventory items 112 may be stored on some of the shelves of the furniture unit 104, while other shelves of the furniture unit 104 do not store inventory items 112.

The imaging and tracking device 102 includes an image sensor, a processing component configured to process data captured using the image sensor, a network interface for communicating information processed using the processing component to other devices (e.g., the server 106), and a power source for supplying power for use by the image sensor, the processing component, and the network interface. The imaging and tracking device 102 monitors activity occurring with respect to the furniture unit 104, such as to detect when an inventory item 112 is removed from the furniture unit 104 and to identify the inventory item 112 which was removed. In some implementations, the imaging and tracking device 102 may use sensors other than an image sensor to detect and identify removed inventory items 112. For example, the imaging and tracking device 102 may include a motion sensor. In another example, the imaging and tracking device 102 include an accelerometer or other sensor capable of detecting vibrations to which the furniture unit 104 is exposed. In yet another example, the imaging and tracking device 102 may include another sensor usable to detect changes within the furniture unit 104.

The imaging and tracking device 102 is removably coupled to a portion of the furniture unit 104. For example, the imaging and tracking device 102 may be coupled to a portion of the furniture unit 104 using a hook and loop fastener, an adhesive strip, a mounting mechanism which enables the removal of the imaging and tracking device 102 from the furniture unit 104, or another removable coupling technique. Alternatively, the imaging and tracking device 102 may be permanently coupled to a portion of the furniture unit 104. For example, the imaging and tracking device 102 may be installed using screws or other mechanical fasteners, an adhesive, a mounting mechanism which prevents the removal of the imaging and tracking device 102 from the furniture unit 104, or another permanent coupling technique.

The server 106 is a computing aspect that runs the software application 108. The server 106 may be or include a hardware server (e.g., a server device), a software server (e.g., a web server and/or a virtual server), or both. For example, where the server 106 is or includes a hardware server, the server 106 may be a server device located in a rack, such as of a data center.

The software application 108 is used to process information received from the imaging and tracking device 102, for example, over a network 116. In some implementations, the software application 108 can be used to process information received from the imaging and tracking device 102 to identify an inventory item 112 which has been physically retrieved from the furniture unit 104. In some implementations, the software application 108 can be used to update database records associated with retrieved inventory items 112. In some implementations, the software application 108 can be used to transmit signals indicative of updated database records to a client 116. In some implementations, the software application 108 is a web application run within a web page served by server 106 and accessed, for example, by the client 116. In some implementations, the software application 108 is a mobile application which includes a server-side application running on the server 106 and a client-side application running on the client 116.

The software application 108 accesses the database 110 stored on the server 106 to perform at least some of the functionality of the software application 108. The database 110 is a database or other data store used to store, manage, or otherwise provide data used to deliver functionality of the web application 108. The database 110 may, for example, be a relational database management system, an object database, an XML database, a configuration management database, a management information base, one or more flat files, other suitable non-transient storage mechanisms, or a combination thereof.

The database 110 can store records relating to inventory supplies (e.g., the inventory 112) which are or may be monitored using the imaging and tracking device 102 or by a different imaging and tracking device within the furniture unit 104 or within a different furniture unit. The database 110 can also store records relating to the usage, including pre-care and post-care instructions, for some or all of the inventory 112. The database 110 can also store records related to administrative tasks, patient-related tasks, patient names, staff members authorized to retrieve the inventory items 112 from the furniture unit 104, and/or other records.

The software application 108 includes a dashboard which enables a user thereof (e.g., a user of the server 106 or a user of the client 116) to review information processed using the system 100. For example, the dashboard can be used to review information received at the software application 108 from the imaging and tracking device 102. In another example, the dashboard can be used to review changes made to records within the database 110 based on the information received from the imaging and tracking device 102. In yet another example, the dashboard can be used to view information (e.g., knowledgebase articles or the like) associated with inventory items 112 which have been detected as being physically retrieved from the furniture unit 104.

The imaging and tracking device 102 communicates with the server 106 over the network 114. The network 114 may, for example, be a local area network, a wide area network, a machine-to-machine network, a virtual private network, or another public or private network. Communication over the network 114 may use one or more network protocols, such as using Ethernet, TCP, IP, power line communication, Wi-Fi, Bluetooth®, infrared, GPRS, GSM, CDMA, Z-Wave, ZigBee, another protocol, or a combination thereof.

The client 116 may be given access to the software application 108. The client 116 may be or include a hardware client (e.g., a client device), a software client (e.g., a web server and/or a virtual server), or both. For example, the client 116 may be a mobile device, such as a smart phone, tablet, laptop, or the like. In another example, the client 116 may be a desktop computer or another non-mobile computer. The client 118 may run a client-side software application or other software to communicate with the software application 108. For example, the client-side software application may be a mobile application that enables access to some or all functionality and/or data of the software application 108. The client 118 communicates with the server 106 over the network 116.

Implementations of the real-time health care inventory imaging and tracking intelligence system 100 may differ from what is shown and described with respect to FIG. 1. In some implementations, the imaging and tracking device 102 communicates with the server 106 over the network 114 using an intermediary relay. For example, the intermediary relay may be or include network hardware, such as a router, a switch, a load balancer, another network device, or a combination thereof. The intermediary relay may receive information and/or commands from and/or transmit information and/or commands to the imaging and tracking device 102 using one or more network protocols, such as using Ethernet, TCP, IP, power line communication, Wi-Fi, Bluetooth®, infrared, GPRS, GSM, CDMA, Z-Wave, ZigBee, another protocol, or a combination thereof.

In some implementations, the server 106 and the client 116 may each represent computing devices located within a common area. For example, the server 106 and the client 116 may both be computers located within a health care clinic or hospital. In some implementations, the server 106 and the client 116 may be combined into a single computing device. In some implementations, the software application 108 may transmit push notifications, text messages, or other alerts to client 116 without client 116 first accessing the software application 108 (e.g., via a webpage or otherwise). For example, the software application 108 can be configured to automatically transmit signals to certain clients, such as using a whitelist or otherwise.

In some implementations, a health care facility may use multiple imaging and tracking devices. For example, each of the multiple imaging and tracking devices may be coupled to a different furniture unit or to different shelves, drawers, or cabinets of the same furniture unit. The software application 108 can be used to receive and process signals from each of the multiple imaging and tracking devices. For example, the software application 108 can identify individual imaging and tracking devices from which data is received, such as within a GUI generated by the software application 108 based on the retrieval of an inventory item 112.

Figure 2:
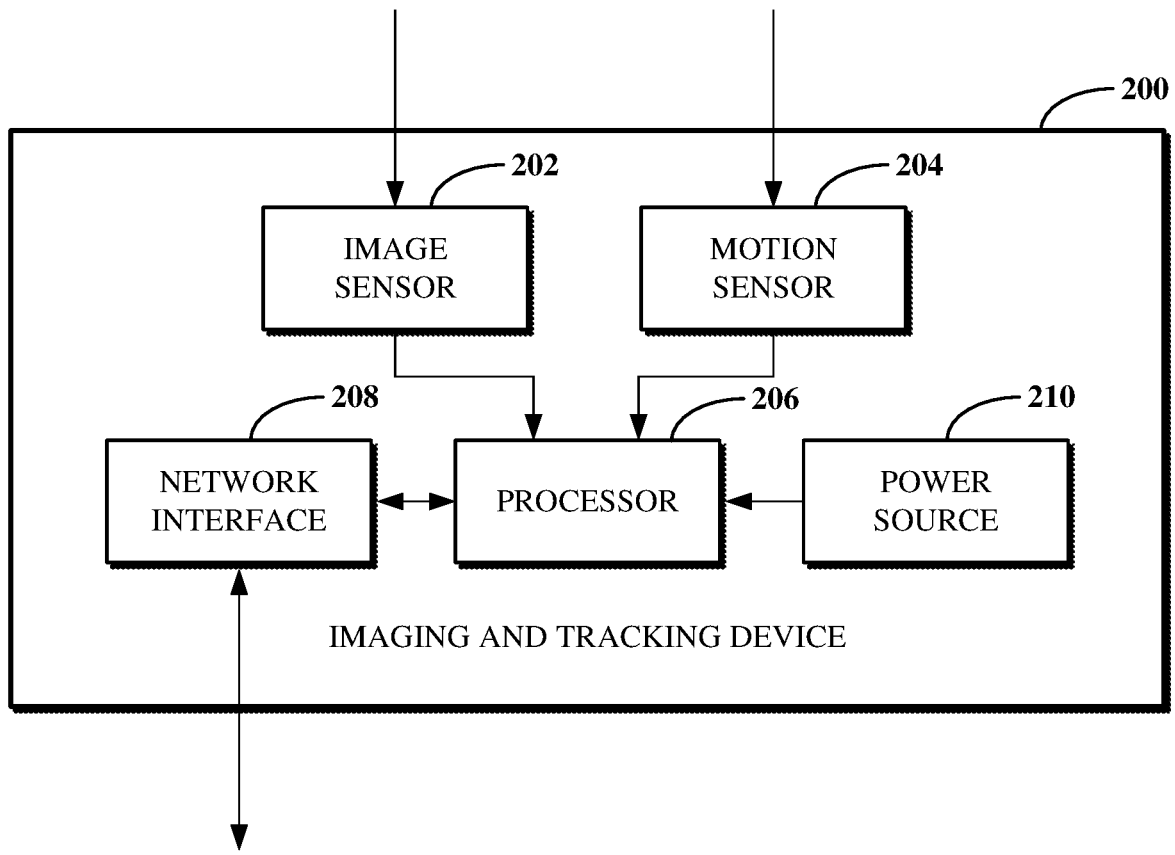
FIG. 2 is a block diagram showing an example of an imaging and tracking device used in a real-time health care inventory imaging and tracking intelligence system.

FIG. 2 is a block diagram showing an example of an imaging and tracking device 200 used in a real-time health care inventory imaging and tracking intelligence system, for example, the system 100 shown in FIG. 1. For example, the imaging and tracking device 200 may be the imaging and tracking device 102 shown in FIG. 1. The imaging and tracking device 200 includes an image sensor 202, a motion sensor 204, a processor 206, a network interface 208, and a power source 210.

The image sensor 202 is a sensor configured to capture images within a field of view of the image sensor 202 or otherwise capture data used to construct images. The image sensor 202 may, for example, be a charge-coupled device sensor, an active pixel sensor, a complementary metal-oxide semiconductor sensor, an N-type metal-oxide-semiconductor sensor, or another sensor or combination of sensors.

The motion sensor 204 is a sensor configured to detect motion within a field of motion of the motion sensor 204.

The motion sensor 204 may, for example, be an infrared sensor (e.g., a passive infrared sensor), a microwave sensor, an area reflective sensor, an ultrasonic sensor, or another sensor or combination of sensors.

The processor 206 is a central processing unit, such as a microprocessor, and can include single or multiple processors having single or multiple processing cores. In some implementations, the processor 206 may be or otherwise refer to an integrated circuit, for example, a field programmable gate array (e.g., FPGA), programmable logic device (PLD), reconfigurable computer fabric (RCF), system on a chip (SoC), an application specific integrated circuit (ASIC), and/or another type of integrated circuit. The processor 206 includes a cache, or cache memory, for local storage of operating data and/or instructions. For example, the cache can be used to temporarily store data recorded using the image sensor 202, the motion sensor 204, and/or another sensor (e.g., in implementations in which the imaging and tracking device 200 includes such another sensor, such as described below).

The network interface 208 is used to transmit information and/or commands to and/or receive information and/or commands from one or more devices external to the imaging and tracking device 200. The network interface 208 provides a connection or link to a network (e.g., the network 114 shown in FIG. 1). The network interface 208 can be a wired network interface or a wireless network interface. The imaging and tracking device 200 can communicate with other devices via the network interface 208 using one or more network protocols, such as using Ethernet, TCP, IP, power line communication, Wi-Fi, Bluetooth, infrared, GPRS, GSM, CDMA, Z-Wave, ZigBee, another protocol, or a combination thereof.

The power source 210 is a source for providing power to the imaging and tracking device 200. For example, the power source 210 can be an interface to an external power distribution system. In another example, the power source 210 can be a battery, such as a coin-cell battery or another battery.

Implementations of the imaging and tracking device 200 may differ from what is shown and described with respect to FIG. 2. In some implementations, the motion sensor 204 may be omitted. In some implementations, one or more other sensors may be included. For example, in some such implementations, the imaging and tracking device 200 may include an accelerometer or other sensor capable of detecting vibrations. The accelerometer or other sensor may be used to monitor for vibrations (e.g., indicative of a person accessing a furniture unit to which the imaging and tracking device 200 is coupled, such as by the person opening a door or pulling on a drawer or shelf of the furniture unit).

The implementation of the imaging and tracking device 200 shown in FIG. 2 includes each of the image sensor 202, the motion sensor 204, the processor 206, the network interface 208, and the power source 210 as being included within a single housing or other enclosure. However, in some implementations, the components of the imaging and tracking device 200 may be physically separated into multiple housings or other enclosures, or otherwise separated. For example, in some such implementations, the image sensor 202 and the motion sensor 204 may be included in a first portion of the imaging and tracking device 200 and the processor 206 and the network interface 208 may be included in a second portion of the imaging and tracking device 200. The first portion may be coupled to the furniture unit. The second portion may be external to the furniture unit.

In some implementations, the power source 210 can cause the network interface 208 transmit a signal indicating a low power status of the imaging and tracking device 200. For example, a server device running a software application (e.g., the server device 106 and the software application 108 shown in FIG. 1)) can receive a signal indicating a low power status of the imaging and tracking device 200. The software application can then indicate the low power status, such as to one or more client devices of personnel of the health care provider that uses the imaging and tracking device 200.

Figure 3:
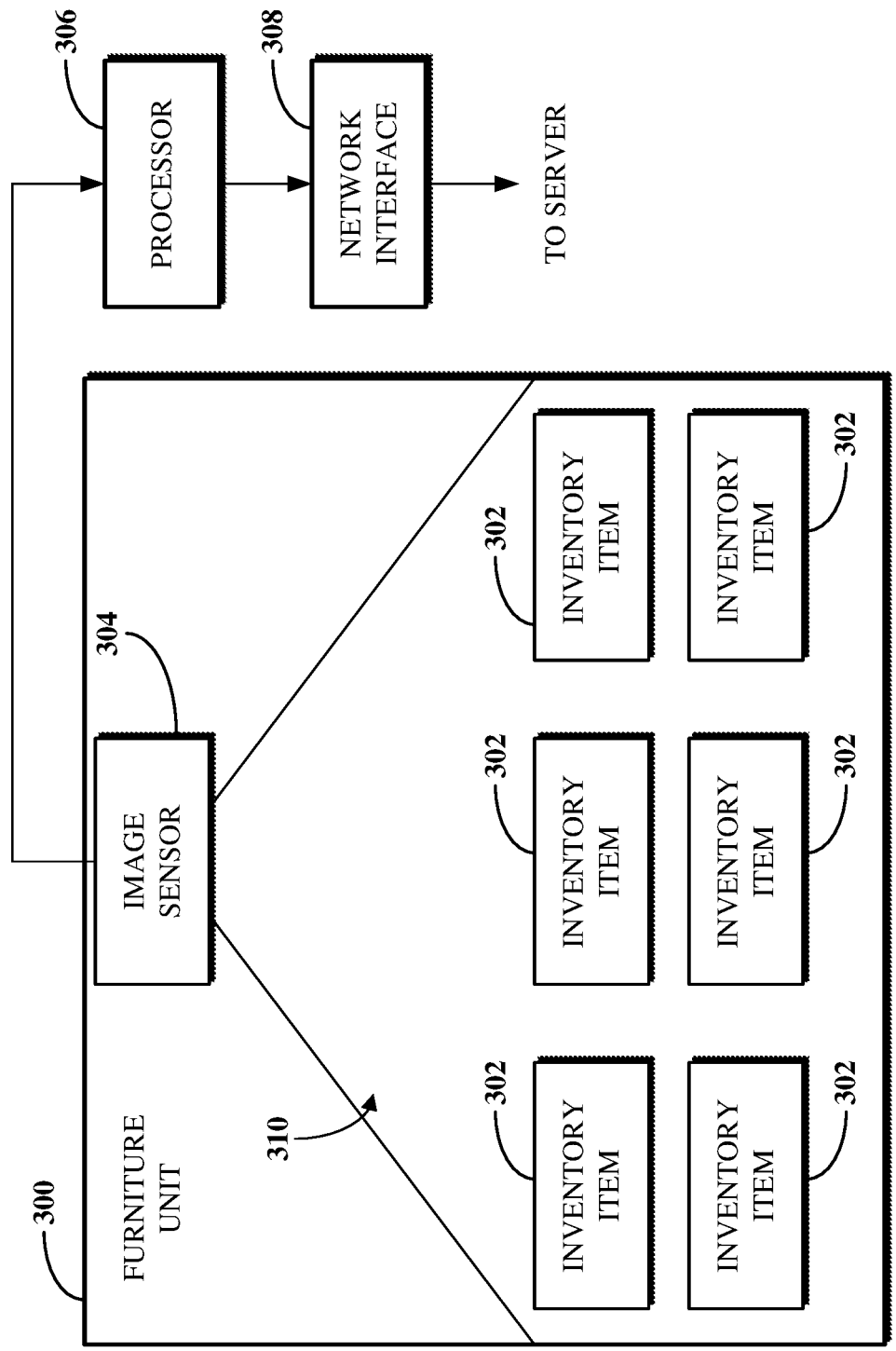
FIG. 3 is a block diagram showing an example of an imaging and tracking device coupled to a furniture unit for monitoring and tracking inventory items.

FIG. 3 is a block diagram showing an example of an imaging and tracking device coupled to a furniture unit 300 for monitoring and tracking inventory items 302. In particular, an image sensor 304, a processor 306, and a network interface 308 of the imaging and tracking device are shown. The image sensor 304, the processor 306, and the network interface 308 may, for example, respectively be the image sensor 202, the processor 206, and the network interface 208 shown in FIG. 2. In the implementation shown in FIG. 3, the image sensor 304 is coupled to the furniture unit 300, and the processor 306 and the network interface 308 are external to the furniture unit 300.

The image sensor 304 has a field of view 310. The field of view 310 represents the physical area of the furniture unit 300 for which the image sensor 304 is configured to capture images. In some implementations, the field of view 310 may be adjustable, such as by selectively opening or narrowing aspects of the image sensor. In some implementations, the image sensor may be included in a controllable mechanism. For example, a user of a software application that processes information received from the imaging and tracking device may use the software application to remotely control, in real-time, a direction of the image sensor 304. Changing the direction of the image sensor 304 causes the specific location of the field of view 310 to change.

Implementations of the imaging and tracking device may differ from what is shown and described with respect to FIG. 3. In some implementations, one or more sensors external to the image sensor 304 may be coupled to the furniture unit 300. For example, the one or more sensors may include weight or pressure sensors configured to detect differences in an amount of weight or pressure applied to a surface on which the inventory items 302 are stored. Such a weight or pressure sensor can be used to detect the physical retrieval of one or more of the inventory items 302. For example, the data recorded using such a weight or pressure sensor can be processed by the processor 306 to detect the physical retrieval of an inventory item 302. In some such implementations, a single weight or pressure sensor may be configured to measure changes in weight or pressure for the entire surface of the furniture unit 300. In other such implementations, multiple weight or pressure sensors may each be disposed in a different location about the surface of the furniture unit 300 and configured to measure changes in weight or pressure for their specific locations.

In some implementations, a light source may be used to illuminate all or a portion of the furniture unit 300. For example, where the furniture unit 300 is or includes an enclosed piece of furniture, the image sensor 304 may not be exposed to enough light to effectively capture images for detecting retrievals of the inventory items 302. In some such implementations, the image sensor 304 and the light source may be included in a common housing or other enclosure.

Figure 4A:
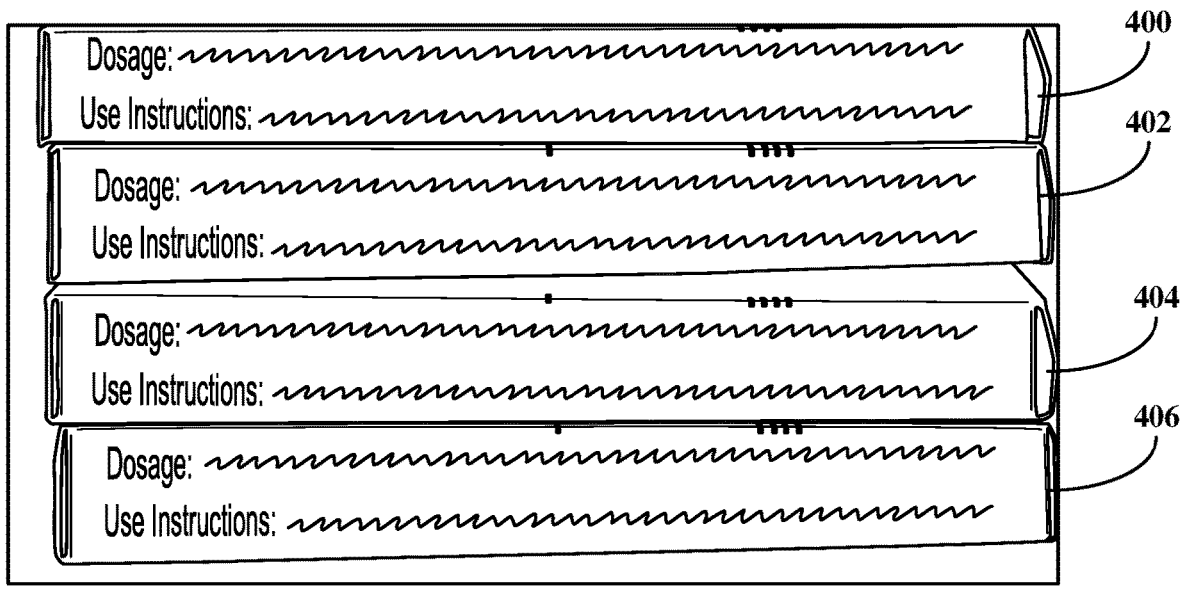
FIGS. 4A-B are illustrations showing examples of inventory item enumeration for identification using an imaging and tracking device.
Figure 4B:
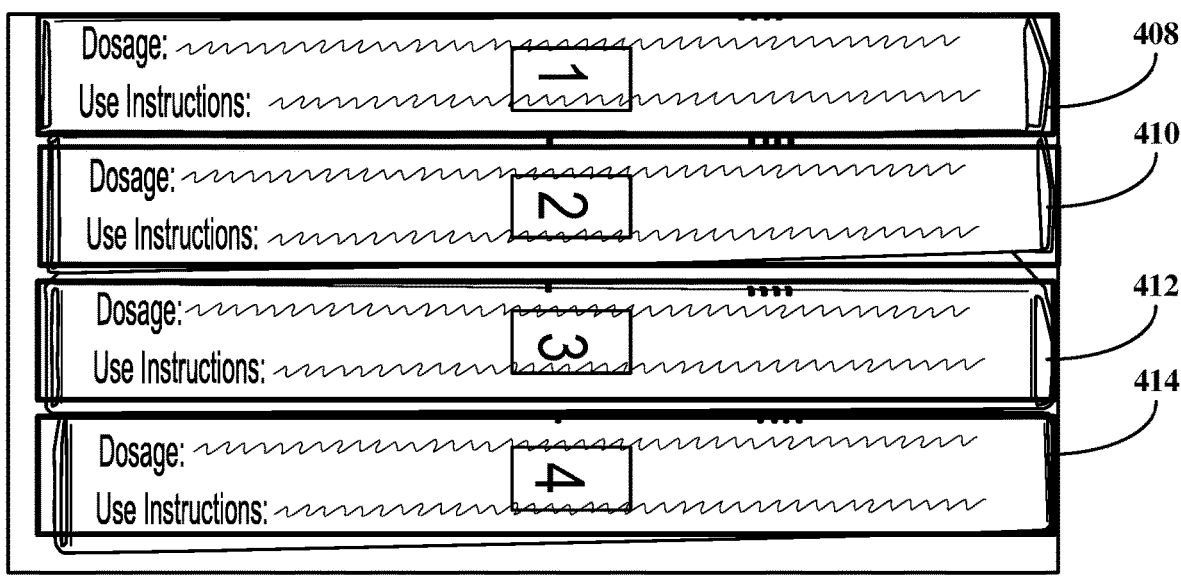

FIGS. 4A-B are illustrations showing examples of inventory item enumeration for identification using an imaging and tracking device. An imaging and tracking device (e.g., the imaging and tracking device 200 shown in FIG. 2) may be configured to detect one or more visual characteristics of some or all inventory items stored within or on a furniture unit. The imaging and tracking device may further be configured to enumerate the detected characteristics and use those enumerations to detect changes within a field of view of an image sensor of the imaging and tracking device.

First, in FIG. 4A, four inventory items 400-406 are shown. The inventory items 400-406 are stored within the same furniture unit. Next, in FIG. 4B, the same inventory items from FIG. 4A are shown with enumerations 408-414. The enumerations 408-414 are visually represented based on detected shapes of the inventory items 400-406 and with annotated numbers representing a total count of the inventory items 400-406, in which the enumerations 408-414 assign each inventory item 400-406 with a number of the total count (e.g., one, two, three, or four, as shown).

The imaging and tracking device can determine that an inventory item has been physically retrieved from the furniture unit based on the enumerations 408-414. For example, enumerations of a first image captured using the image sensor of the imaging and tracking device may indicate that all four of the inventory items 400-406 are present at the time the first image was captured. However, enumerations of a second image captured using the image sensor of the imaging and tracking device at a time after the first image was captured may indicate that only three of the inventory items 400-406 remain within or on the furniture unit.

Based on this information, the imaging and tracking device can determine that one of the four inventory items 400-406 has been physically retrieved from the furniture unit. The imaging and tracking device can then determine which of the four inventory items 400-406 the retrieved inventory item is. The imaging and tracking device can then generate a signal indicating information identifying the retrieved inventory item and transmit that signal to a server running a software application (e.g., the server 106 and the software application 108 shown in FIG. 1) to cause the software application to update a database record (e.g., of the database 110 shown in FIG. 1) associated with the retrieved inventory item.

Figure 5:
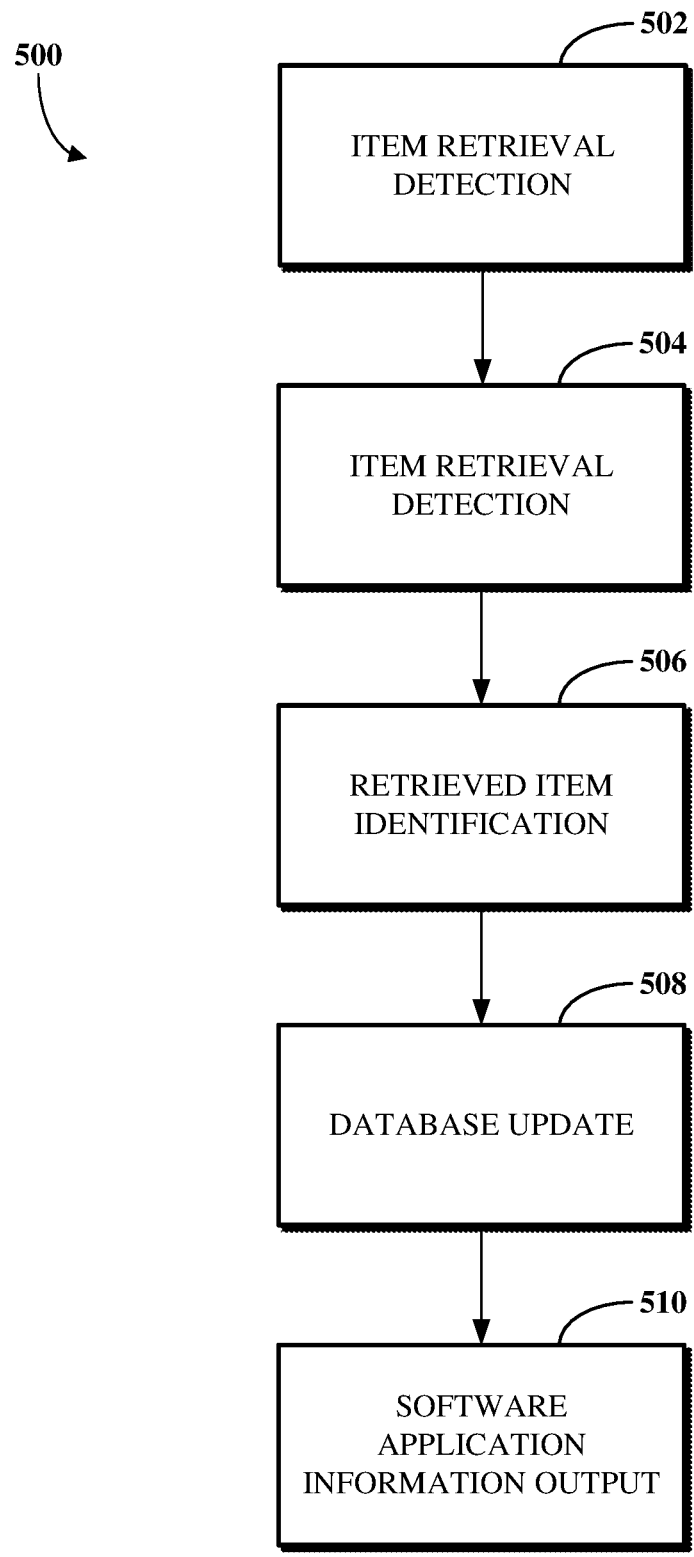
FIG. 5 is a block diagram showing an example of a workflow of a real-time health care inventory imaging and tracking intelligence system.

FIG. 5 is a block diagram showing an example of a workflow 500 of a real-time health care inventory imaging and tracking intelligence system. The workflow 500 commences at 502 with a health care provider creating a task for performance within a software application of a real-time health care inventory imaging and tracking intelligence system (e.g., the software application 108 of the system 100 shown in FIG. 1). Based on the created task, the health care provider looks for an inventory item to use to perform the task. At 504, after the health care provider retrieves the inventory item from the furniture unit, the imaging and tracking device corresponding to that furniture unit detects the physical retrieval of the inventory item.

At 506, the retrieved inventory item is identified. Identifying the retrieved inventory item includes identifying or otherwise determining information usable to identify the retrieved inventory item, such as from amongst the other inventory items stored within the same furniture unit or otherwise used at the same health care facility. The retrieved inventory item can be identified by the imaging and tracking device used to detect the retrieval of the inventory item from the respective furniture unit and/or by the software application that receives a signal from the imaging and tracking device. At 508, a database accessed by the software application is updated to indicate the retrieval of the inventory item. For example, updating the database can include updating a record associated with an inventory of the inventory item to indicate that the total inventory for that inventory item type has decreased. At 510, the software application outputs information indicative of the updated database record. For example, the software application can output information to a dashboard of the software application, which may, for example, be included in a GUI of the software application.

Implementations of the workflow 500 may differ from what is shown and described with respect to FIG. 5. In some implementations, after the health care provider retrieves the inventory item, the health care provider can submit information identifying the retrieved inventory item to the software application. For example, the health care provider can scan a barcode or other coded portion of the inventory item or otherwise indicate the inventory item to the software application. The software application can use the submitted information in one or more ways. In some implementations, the software application can use the submitted information to verify the automated detection and identification of the retrieved inventory item by the imaging and tracking device and/or by the software application. In some implementations, the software application can correlate the submitted application to the task created at the beginning of the workflow 500. In some implementations, the software application can use the submitted information to train a machine learning model (e.g., a neural network or other intelligence approach) to recognize the retrieved inventory item.

In some implementations, the workflow 500 further includes inventory analytics. For example, the software application can include functionality for performing predictive analytics against information, such as database records stored within the database (e.g., the database 110). In some such implementations, the predictive analytics can include using a model (e.g., a machine learning model or another model) to analyze trends in inventory item usage over time. For example, the trends in inventory item usage over time can be analyzed to forecast inventory requirements for the inventory item and/or to forecast inventory usage for the inventory item over some period of time. In some such implementations, the software application can include functionality for automating re-ordering processes for acquiring more of an inventory item, for example, based on output of the predictive analytics of the software application.

FIG. 6 is an illustration showing an example of a GUI 600 of a software application for inventory tracking and management. The GUI 600 is a GUI which may be rendered or displayed, such as to render or display pages of a software application of a real-time health care inventory imaging and tracking intelligence system for use (e.g., the software application 108 of the system 100 shown in FIG. 1). The GUI 600 can comprise part of a software GUI constituting data that reflect information ultimately destined for display on a hardware device, for example, the client 116 shown in FIG. 1). For example, the data can contain rendering instructions for bounded graphical display regions, such as windows, or pixel information representative of controls, such as buttons and drop-down menus. The rendering instructions can, for example, be in the form of HTML, SGML, JavaScript, Jelly, AngularJS, or other text or binary instructions for generating the GUI 600 or another GUI on a display that can be used to generate pixel information. A structured data output of one device can be provided to an input of the hardware display so that the elements provided on the hardware display screen represent the underlying structure of the output data.

The GUI 600 includes multiple frames, each showing different information of the real-time health care inventory imaging and tracking intelligence system. For example, a first frame 602 shows information specific to a retrieved inventory item. As shown, the information in the first frame 602 includes an identification number, an item name, a tradename, a manufacturer name, a reference number, a lot number, an expiration date, and a shelf location (e.g., indicating the furniture unit of the health care clinic from which the inventory item was retrieved and/or the location at which that inventory item was stored within or on that furniture unit). In another example, a second frame 604 indicates quantities of the inventory item which have been used in recent time. As shown, the second frame 604 includes a textual visualization of the quantities used and a graphical visualization thereof.

In yet another example, a third frame 606 includes some or all of a knowledgebase article associated with the inventory item which has been physically retrieved from a furniture unit. The knowledgebase article can include one or more of a description of the inventory item, instructions for using the inventory item, care instructions for before or after the inventory item is used, storage instructions for the inventory item, or other information associated with the inventory item. The knowledgebase articles may include one or more of text, images, audio, or video. The third frame 600 may include some or all of a knowledgebase article. In some implementations, where only some of the knowledgebase article is shown, the third frame 600 may also include a link to the knowledgebase page which includes that article.

In some implementations, the software application which generates the GUI 600 or otherwise generates the instructions for rendering the GUI 600 can retrieve the knowledgebase article (e.g., from the database 110 shown in FIG. 1) in response to the identification of the retrieved inventory item at the software application. For example, the software application can automatically retrieve some or all of the knowledgebase for a retrieved inventory item in response to receipt of a signal from an imaging and tracking device, such as whether the signal itself identifies the retrieved inventory item or whether the signal includes information used by the software application to identify the retrieved inventory item.

After the knowledgebase article is retrieved, it can be transmitted to a computing device of a health care provider (e.g., a nurse or other clinic or hospital staff) who will use the inventory item (e.g., the client 116 shown in FIG. 1). For example, transmitting the knowledgebase article to the computing device of the health care provider can include the software application generating instructions for displaying the knowledgebase article in the GUI 600 and transmitting those instructions along with the GUI 600 to (or along with instructions for rendering the GUI 600 at) the computing device of the health care provider. The retrieval and transmission of the knowledgebase article is automatic upon the detection and identification of the retrieved inventory item such that no manual user intervention is required to cause the knowledgebase article to be sent to the computing device of the health care provider.

Implementations of the GUI 600 may differ from what is shown and described with respect to FIG. 6. In some implementations, the GUI 600, or another GUI of the software application of the real-time health care inventory imaging and tracking intelligence system, may include a video display. For example, the video display can be used to show enumerations of the inventory items of one or more furniture units by the system. In some such implementations, the GUI 600, or the other GUI which includes the video display, may also display information related to the enumerated inventory items, including, without limitation, expiration dates, reference numbers, lot numbers, manufacturer information, purchase dates, purchase prices, and/or national drug code numbers.

Figure 7:
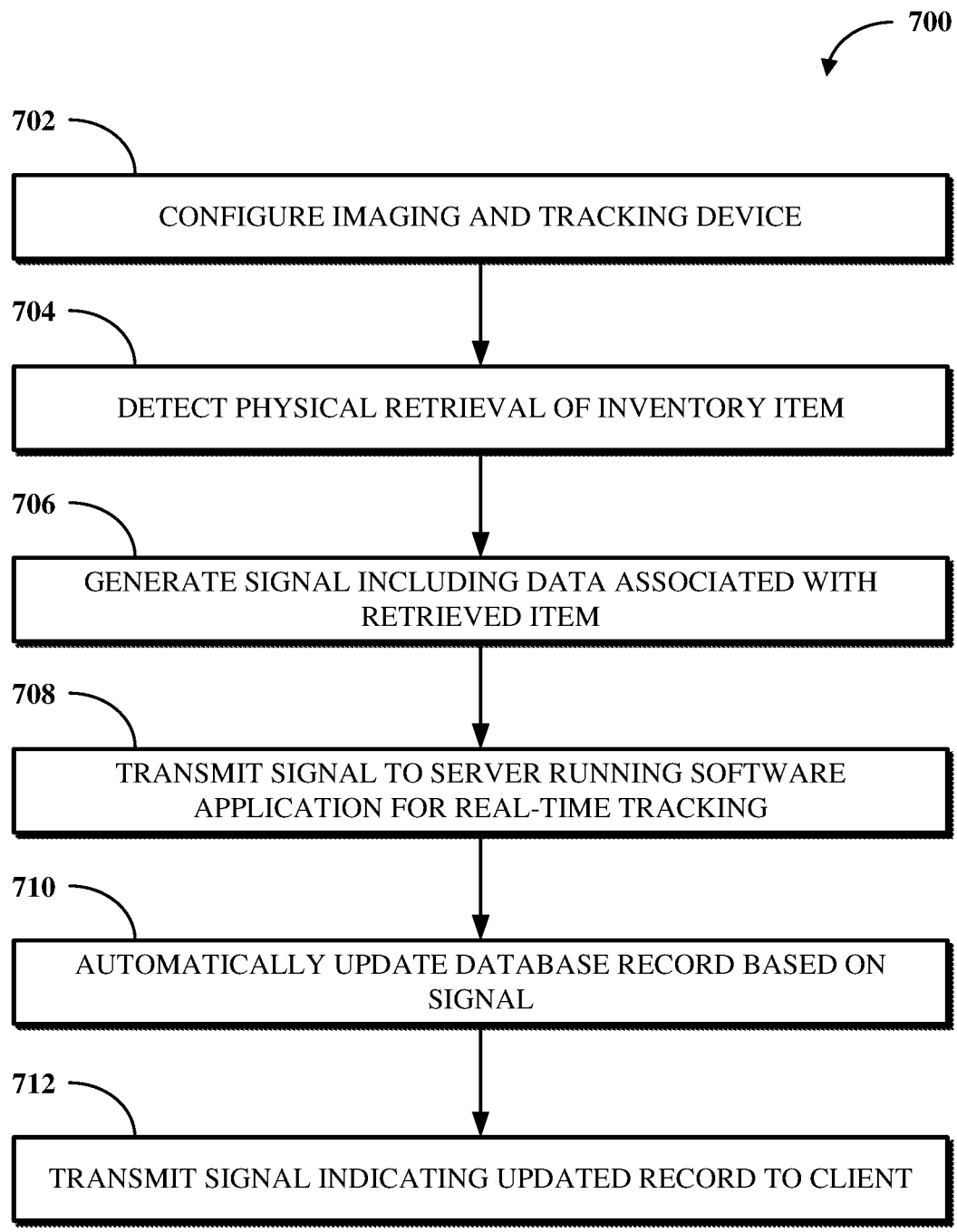
FIG. 7 is a flowchart showing an example of a technique for real-time health care inventory imaging and tracking intelligence.

To further describe some implementations in greater detail, reference is next made to an example of a technique which may be performed by or using a real-time health care inventory imaging and tracking intelligence system as described with respect to FIGS. 1-6. FIG. 7 is a flowchart showing an example of a technique 700 for real-time health care inventory imaging and tracking intelligence. The technique 700 can be executed using computing devices, such as the systems, hardware, and software described with respect to FIGS. 1-6. The technique 700 can be performed, for example, by executing a machine-readable program or other computer-executable instructions, such as routines, instructions, programs, or other code. The steps, or operations, of the technique 700 or another technique, method, process, or algorithm described in connection with the implementations disclosed herein can be implemented directly in hardware, firmware, software executed by hardware, circuitry, or a combination thereof.

For simplicity of explanation, the technique 700 is depicted and described herein as a series of steps or operations. However, the steps or operations in accordance with this disclosure can occur in various orders and/or concurrently. Additionally, other steps or operations not presented and described herein may be used. Furthermore, not all illustrated steps or operations may be required to implement a technique in accordance with the disclosed subject matter.

At 702, the imaging and tracking device is configured for use in tracking inventory items within a furniture unit. Configuring the imaging and tracking device includes coupling at least a portion of the imaging and tracking device to a portion of the furniture unit. The imaging and tracking device can be removably coupled to the furniture unit, for example, to enable easy relocation of the imaging and tracking device. Alternatively, the imaging and tracking device can be permanently coupled to the furniture unit. In some implementations configuring the imaging and tracking device further includes adjusting a field of view of an image sensor of the imaging and tracking device to enable the image sensor to capture an image of each of the inventory items. Adjusting the field of view of the image sensor can include remotely controlling a pan/tilt motor of the image sensor to adjust an orientation of the image sensor. In some implementations, the remote controlling of the pan/tilt motor can be automated by the software application. For example, the software application can automatically adjust the orientation of the image sensor responsive to a determination that a field of view of the image sensor does not capture all or a threshold number of inventory items stored within a furniture unit.

At 704, the imaging and tracking device is used to detect the physical retrieval of one of the inventory items from the furniture unit. Detecting the physical retrieval of the one of the inventory items from the furniture unit can include comparing first image data against second image data. For example, the first image data may include an image generated using the image sensor of the imaging and tracking device before the physical retrieval of the one of the inventory items, and the second image data may include an image generated using the image sensor after the physical retrieval of the one of the inventory items. In some implementations, the retrieval of the inventory item can be detected using enumerations for the first image data and using enumerations for the second image data. For example, the enumerations can be used to determine that an enumerated inventory item is removed from a field of view of the image sensor. In some implementations, the enumerations or data indicative thereof may be stored in a cache of the imaging and tracking device. The imaging and tracking device can retrieve recently cached enumerations or other data and compare such retrieved enumerations or other data to current enumerations or other data to detect a change in the inventory items stored within or on the furniture unit.

At 706, a first signal including data identifying the retrieved inventory item is generated at the imaging and tracking device. The information included in the first signal can be different based on whether the retrieved inventory item is identified at the imaging and tracking device. For example, where the retrieved inventory item is identified at the imaging and tracking device, the first signal can include information identifying the retrieved inventory item. In another example, where the retrieved inventory item is not identified at the imaging and tracking device, the first signal can include information usable by a software application that will process the first signal to identify the retrieved inventory item.

At 708, the first signal is transmitted from the imaging and tracking device to a server device running a software application. Transmitting the first signal from the imaging and tracking device to the server device can including using a network interface of the imaging and tracking device to wirelessly communicate the first signal to the server device over a short-range communication protocol. In some implementations, the short-range communication protocol can be Wi-Fi or Bluetooth®.

At 710, the software application automatically updates a database record associated with the retrieved inventory item based on the first signal. The updating of the database record occurs without manual user intervention. The software application updates the database record by processing the first signal to identify the retrieved inventory item. The software application then queries a database using an identifier of the retrieved inventory item to retrieve a database record associated with the retrieved inventory item from the database. The software application can then update that database record. Updating the database record based on the first signal can include updating one or more pieces of data included in the database record. For example, the data included in the first signal can be used to update data of the database record including, but not limited to, a total inventory number for the inventory item type, a time at which the inventory item was last retrieved, a furniture unit from which the inventory item last retrieved, a task created for performance using the retrieved inventory item, or other information.

At 712, a second signal indicative of the updated database record is transmitted from the server device to a client device. The second signal includes information, instructions, or the like and is used to indicate a user of the client device as to the updated database record. For example, the second signal may include instructions for rendering a GUI at the client device, which GUI includes updated inventory information for the retrieved inventory item and/or some or all of a knowledgebase article indicating use and/or care instructions for the retrieved inventory item. In some implementations, the second signal can be an alert (e.g., a push notification, text message, or other alert) associated with a task to perform using the retrieved inventory item. For example, a health care facility manager can receive the second signal as an alert to indicate that a staff member of the health care facility is performing or has completed performance of a task.

In some implementations, the imaging and tracking device 102 can use different states for power preservation. For example, a wait state can be used to cause a power source of the imaging and tracking device to preserve power, such as by causing a processor of the imaging and tracking device to put the imaging and tracking device into a low-power mode. In another example, an active state can be used to cause the power source to use necessary power to enable the other components of the imaging and tracking device to detect inventory item retrievals and/or generate and communicate signals indicative of such detections.

In some such implementations, the technique 700 may include changing the state of the imaging and tracking device from the wait state to the active state. For example, upon the detection of a vibration, the processor may change the state of the imaging and tracking device from a wait state to an active state, such as to enable the use of the image sensor. In some such implementations, the processor changes the state of the imaging and tracking device in response to a determination that the vibration detected using the accelerometer or other vibration sensor meets a threshold. For example, the threshold may be used to prevent false positive situations in which the furniture unit is exposed to a vibration unrelated to the accessing of the furniture unit.

Figure 8:
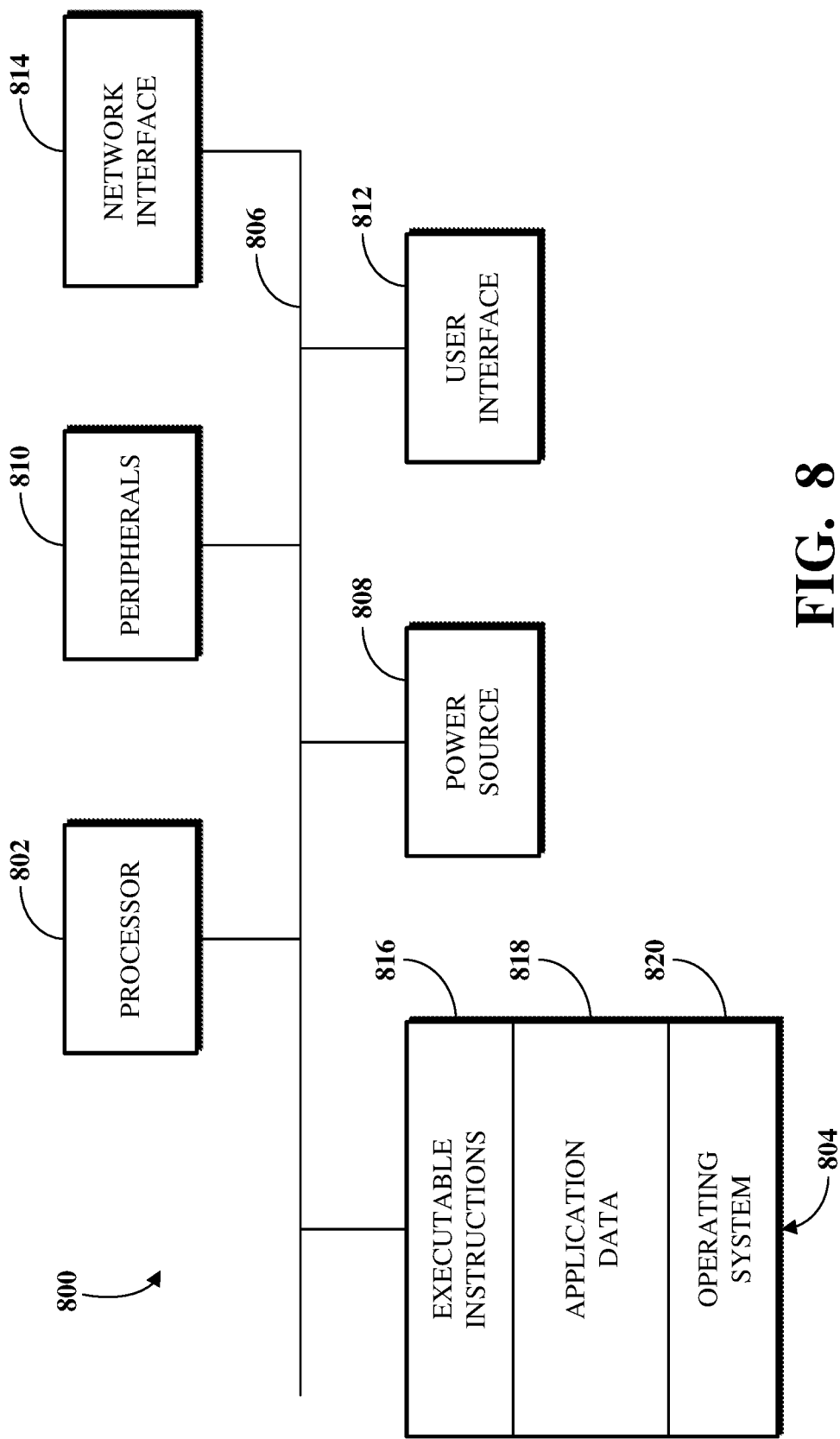
FIG. 8 is a block diagram showing an example of a computing device which may be used in a region-based electrical intelligence system.

FIG. 8 is a block diagram showing an example of a computing device 800 which may be used in a real-time health care inventory imaging and tracking intelligence system, for example, the system 100 shown in FIG. 1. The computing device 800 may be used to implement a server on which a software application is run (e.g., the server 106 and the software application 108 shown in FIG. 1). Alternatively, the computing device 800 may be used to implement a client that accesses the software application (e.g., the client 116 shown in FIG. 1). As a further alternative, the computing device 800 may be used as or to implement another client, server, or other device according to the implementations disclosed herein. The computing device 800 includes components or units, such as a processor 802, a memory 804, a bus 806, a power source 808, peripherals 810, a user interface 812, and a network interface 814. One of more of the memory 804, the power source 808, the peripherals 810, the user interface 812, or the network interface 814 can communicate with the processor 802 via the bus 806.

The processor 802 is a central processing unit, such as a microprocessor, and can include single or multiple processors having single or multiple processing cores. Alternatively, the processor 802 can include another type of device, or multiple devices, now existing or hereafter developed, configured for manipulating or processing information. For example, the processor 802 can include multiple processors interconnected in any manner, including hardwired or networked, including wirelessly networked. For example, the operations of the processor 802 can be distributed across multiple devices or units that can be coupled directly or across a local area or other suitable type of network. The processor 802 can include a cache, or cache memory, for local storage of operating data and/or instructions.

The memory 804 includes one or more memory components, which may each be volatile memory or non-volatile memory. For example, the volatile memory of the memory 804 can be random access memory (RAM) (e.g., a DRAM module, such as DDR SDRAM) or another form of volatile memory. In another example, the non-volatile memory of the memory 804 can be a disk drive, a solid state drive, flash memory, phase-change memory, or another form of non-volatile memory configured for persistent electronic information storage. The memory 804 may also include other types of devices, now existing or hereafter developed, configured for storing data or instructions for processing by the processor 802.

The memory 804 can include data for immediate access by the processor 802. For example, the memory 804 can include executable instructions 816, application data 818, and an operating system 820. The executable instructions 816 can include one or more application programs, which can be loaded or copied, in whole or in part, from non-volatile memory to volatile memory to be executed by the processor 802. For example, the executable instructions 816 can include instructions for performing some or all of the techniques of this disclosure. The application data 818 can include user data, database data (e.g., database catalogs or dictionaries), or the like. The operating system 820 can be, for example, Microsoft Windows®, Mac OS X®, or Linux®, an operating system for a small device, such as a smartphone or tablet device; or an operating system for a large device, such as a mainframe computer.

The power source 808 includes a source for providing power to the computing device 800. For example, the power source 808 can be an interface to an external power distribution system. In another example, the power source 808 can be a battery, such as where the computing device 800 is a mobile device or is otherwise configured to operate independently of an external power distribution system.

The peripherals 810 includes one or more sensors, detectors, or other devices configured for monitoring the computing device 800 or the environment around the computing device 800. For example, the peripherals 810 can include a geolocation component, such as a global positioning system location unit. In another example, the peripherals can include a temperature sensor for measuring temperatures of components of the computing device 800, such as the processor 802.

The user interface 812 includes one or more input interfaces and/or output interfaces. An input interface may, for example, be a positional input device, such as a mouse, touchpad, touchscreen, or the like; a keyboard; or another suitable human or machine interface device. An output interface may, for example, be a display, such as a liquid crystal display, a cathode-ray tube, a light emitting diode display, or other suitable display.

The network interface 814 provides a connection or link to a network (e.g., the network 116 shown in FIG. 1). The network interface 814 can be a wired network interface or a wireless network interface. The computing device 800 can communicate with other devices via the network interface 814 using one or more network protocols, such as using Ethernet, TCP, IP, power line communication, Wi-Fi, Bluetooth, infrared, GPRS, GSM, CDMA, Z-Wave, ZigBee, another protocol, or a combination thereof.

Implementations of the computing device 800 may differ from what is shown and described with respect to FIG. 8. In some implementations, the computing device 800 can omit the peripherals 810. In some implementations, the memory 804 can be distributed across multiple devices. For example, the memory 804 can include network-based memory or memory in multiple clients or servers performing the operations of those multiple devices. In some implementations, the application data 818 can include functional programs, such as a web browser, a web server, a database server, another program, or a combination thereof.

The implementations of this disclosure can be described in terms of functional block components and various processing operations. Such functional block components can be realized by a number of hardware or software components that perform the specified functions. For example, the disclosed implementations can employ various integrated circuit components (e.g., memory elements, processing elements, logic elements, look-up tables, and the like), which can carry out a variety of functions under the control of one or more microprocessors or other control devices. Similarly, where the elements of the disclosed implementations are implemented using software programming or software elements, the systems and techniques can be implemented with a programming or scripting language, such as C, C++, Java, JavaScript, assembler, or the like, with the various algorithms being implemented with a combination of data structures, objects, processes, routines, or other programming elements.

Functional aspects can be implemented in algorithms that execute on one or more processors. Furthermore, the implementations of the systems and techniques disclosed herein could employ a number of conventional techniques for electronics configuration, signal processing or control, data processing, and the like. The words "mechanism" and "component" are used broadly and are not limited to mechanical or physical implementations, but can include software routines in conjunction with processors, etc.

Likewise, the terms "system" or "mechanism" as used herein and in the figures, but in any event based on their context, may be understood as corresponding to a functional unit implemented using software, hardware (e.g., an integrated circuit, such as an ASIC), or a combination of software and hardware. In certain contexts, such systems or mechanisms may be understood to be a processor-implemented software system or processor-implemented software mechanism that is part of or callable by an executable program, which may itself be wholly or partly composed of such linked systems or mechanisms.

Implementations or portions of implementations of the above disclosure can take the form of a computer program product accessible from, for example, a computer-usable or computer-readable medium. A computer-usable or computer-readable medium can be any device that can, for example, tangibly contain, store, communicate, or transport a program or data structure for use by or in connection with any processor. The medium can be, for example, an electronic, magnetic, optical, electromagnetic, or semiconductor device.

Other suitable mediums are also available. Such computer-usable or computer-readable media can be referred to as non-transitory memory or media, and can include volatile memory or non-volatile memory that can change over time. A memory of an apparatus described herein, unless otherwise specified, does not have to be physically contained by the apparatus, but is one that can be accessed remotely by the apparatus, and does not have to be contiguous with other memory that might be physically contained by the apparatus.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system, comprising:
a server device running a software application, wherein the software application is configured to receive an identification of a health care task to be performed using an inventory item; and
an imaging and tracking device removably coupled to an interior surface of a furniture unit enclosed by a door, the imaging and tracking device including an image sensor, one or more other sensors, and a processor, wherein the imaging and tracking device changes from a wait state to an active state based on sensor measurements produced using the one or more other sensors meeting a threshold, wherein, to preserve resources, the imaging and tracking device in the wait state restricts image capture using the image sensor and in the active state captures images of inventory items stored within the furniture unit using the image sensor, and wherein:
the image sensor captures a first image of inventory items stored within the furniture unit at a first time, the inventory items including a first subset of inventory items and a second subset of inventory items;
the processor detects one or more visual characteristics of the inventory items based on the first image to determine that all of the first subset of inventory items are of a given item type and that the second subset of inventory items includes items are other than of the given item type;
the processor assigns enumerations to the first subset of inventory items within the first image according to the one or more visual characteristics of the inventory items to determine a first count of enumerations of the first subset of inventory items;
the one or more other sensors produce first sensor measurements representative of a vibration detected at the furniture unit at a second time after the first time;
the processor determines for the imaging and tracking device to remain in the wait state responsive to a determination that the first sensor measurements do not meet the threshold;
the one or more other sensors produce second sensor measurements representative of a vibration detected at the furniture unit at a third time after the second time;
the processor determines to change the imaging and tracking device to the active state responsive to a determination that the second sensor measurements meet the threshold;
the image sensor captures a second image of the inventory items based on the change to the active state;
the processor processes the second image to detect a physical retrieval of one of the first subset of inventory items from the furniture unit based on a second count of enumerations of the first subset of inventory items determined based on the second image not matching the first count of enumerations of the first subset of inventory items, wherein the retrieved inventory item corresponds to the inventory item in the health care task to be performed;
the processor sends the first signal to the server device including data associated with a retrieved inventory item responsive to the physical retrieval of the retrieved inventory item; and
the server device updates a database record associated with the retrieved inventory item within a database responsive to the first signal, and transmits a second signal to a client device in communication with the server device responsive to the first signal, wherein the second signal includes an alert that the health care task is being performed with the retrieved inventory item, and wherein the second signal includes information associated with the updated database record.

2. The system of claim 1, wherein the information associated with the updated database record includes instructions for rendering a graphical user interface of the software application at the client device, wherein the graphical user interface displays information associated with the retrieved inventory item and the information associated with the updated database record.

3. The system of claim 2, wherein the information displayed within the graphical user interface includes a knowledgebase article describing instructions for using the retrieved inventory item, wherein the graphical user interface is output for display at the client device in response to the updating of the database record.

4. The system of claim 1, wherein the imaging and tracking device includes a motor used to adjust an orientation of the image sensor, wherein the software application is configured to automatically control the motor based on a field of view of the image sensor.

5. The system of claim 1, wherein the data included in the signal includes data recorded using the image sensor and data recorded using the one or more other sensors.

6. An imaging and tracking device, comprising:
an image sensor configured to capture images of inventory items stored within a furniture unit to which at least a portion of the imaging and tracking device is coupled when the imaging and tracking device is in an active state;
one or more other sensors configured to produce sensor measurements used to determine whether to change the imaging and tracking device from a wait state to the active state, wherein resources of the imaging and tracking device are preserved while in the wait state;
a processor configured to:
process a first image captured using the image sensor at a first time to assign enumerations to a subset of the inventory items based on detected characteristics of the subset of the inventory items being of a same item type,
determine for the imaging and tracking device to remain in the wait state responsive to first sensor measurements produced by the one or more other sensors at a second time after the first time not meeting a threshold, wherein resources of the imaging and tracking device are preserved while in the wait state by the imaging and tracking device restricting image capture using the image sensor while in the wait state,
determine for the imaging and tracking device to change to the active wait state responsive to second sensor measurements produced by the one or more other sensors at a third time after the second time meeting the threshold,
cause the image sensor to capture a second image responsive to the change to the active state,
process the second image to detect a physical retrieval of one of the subset of the inventory items from the furniture unit based on a second count of enumerations of the subset of the inventory items determined based on the second image not matching a first count of enumerations of the subset of the inventory items, and generate a signal including data identifying the retrieved inventory item, wherein the retrieved inventory item corresponds to a health care task previously received at a server device to be performed with an inventory item; and a network interface that transmits the signal to the server device, wherein a software application running on the server device uses the signal to cause an automatic update to a record associated with the retrieved inventory item within a database and generate an alert to a client device indicating that the health care task is being performed with the retrieved inventory item.

7. The imaging and tracking device of claim 6, further comprising:

a motion sensor that detects movements proximate to the inventory items, wherein the processor uses the movements to detect the physical retrieval of the one of the subset of the inventory items from the furniture unit.

8. The imaging and tracking device of claim 6, further comprising:

a power source that powers the imaging and tracking device, wherein the power source preserves power when the imaging and tracking device is in the wait state.

9. The imaging and tracking device of claim 6, further comprising:

a light source that illuminates the furniture unit for the image sensor to capture the images.

10. The imaging and tracking device of claim 6, wherein the enumerations of the inventory items include annotated numbers representing a total count of the subset of the inventory items in which the enumerations assign each of the inventory items a number of the total count.

11. The imaging and tracking device of claim 6, wherein the detected characteristics of the inventory items correspond to detected shapes of the inventory items.

12. The imaging and tracking device of claim 6, wherein a first portion of the imaging and tracking device includes the image sensor and is coupled to a portion of the furniture unit, wherein a second portion of the imaging and tracking device includes the processor and is external to the furniture unit, wherein data is wirelessly communicated between the image sensor and the processor using a short-range communication protocol.

13. A method, comprising:

receiving, at a server device, an indication of a health care task to be performed using an inventory item;

capturing, using an image sensor of an imaging and tracking device coupled to a furniture unit, a first image of inventory items stored within the furniture unit at a first time;

detecting, using a processor of the imaging and tracking device, one or more visual characteristics of the inventory items the first image to determine that a subset of the inventory items are all of a given item type;

determining a first count of enumerations of the subset of the inventory items;

determining, using the processor of the imaging and tracking device, for the imaging and tracking device to remain in a wait state based on first sensor measurements produced using one or more sensors of the imaging and tracking device and representing a vibration detected at the furniture unit at a second time after the first time not meeting a threshold, wherein resources of the imaging and tracking device are preserved while in the wait state by the imaging and tracking device restricting image capture using the image sensor while in the wait state;

determining, using the processor of the imaging and tracking device, for the imaging and tracking device to change from the wait state to an active state based on second sensor measurements produced using one or more other sensors of the imaging and tracking device and representing a vibration detected at the furniture unit at a third time after the second time meeting the threshold;

capturing, using the image sensor of the imaging and tracking device, a second image based on the change from the wait state to the active state;

detecting, using the processor of the imaging and tracking device, a physical retrieval of one of the subset of the inventory items from the furniture unit based on a second count of enumerations of the subset of the inventory items determined based on the second image not matching the first count of enumerations of the subset of the inventory items;

generating, using the processor of the imaging and tracking device, a signal including data associated with the retrieved inventory item, wherein the retrieved inventory item is associated with the inventory item in the health care task to be performed;

transmitting, from the imaging and tracking device, the signal to the server device, wherein the server device runs a software application to cause an automatic update to a database record associated with the retrieved inventory item; and generating, by the server device, an alert to a client device indicating that the health care task is being performed with the retrieved inventory item.

14. The method of claim 13, the method comprising:

adjusting a field of view of an image sensor of the imaging and tracking device to enable the image sensor to capture an image of each of the inventory items.

15. The method of claim 14, wherein the imaging and tracking device is removably coupled to the furniture unit.

16. The method of claim 14, wherein a first portion of the imaging and tracking device is coupled to a portion of the furniture unit and a second portion of the imaging and tracking device is external to the furniture unit.

17. The method of claim 16, wherein the first portion of the imaging and tracking device includes the image sensor and the second portion of the imaging and tracking device includes a network interface, wherein data is wirelessly communicated between the image sensor and the network interface using a short-range communication protocol.

18. The method of claim 13, the method comprising:

assigning, using the processor of the imaging and tracking device, enumerations to the subset of the inventory items based on the one or more visual characteristics, wherein the enumerations of the subset of the inventory items include annotated numbers representing a total count of the subset of the inventory items in which the enumerations assign each of the subset of the inventory items a number of the total count.

19. The method of claim 13, wherein the one or more visual characteristics of the inventory items correspond to detected shapes of the subset of the inventory items.

20. The method of claim 13, wherein a machine learning model is trained to recognize the inventory items, and wherein the data associated with the retrieved inventory item includes data output from the machine learning model.

* * * * *